US007479538B2

United States Patent
Zhabilov

(10) Patent No.: US 7,479,538 B2
(45) Date of Patent: *Jan. 20, 2009

(54) IRREVERSIBLY-INACTIVATED PEPSINOGEN FRAGMENT AND PHARMACEUTICAL COMPOSITIONS COMPRISING THE SAME FOR DETECTING, PREVENTING, AND TREATING HIV

(75) Inventor: Harry H. Zhabilov, San Marino, CA (US)

(73) Assignee: The Zhabilov Trust, San Marino, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 11/177,427

(22) Filed: Jul. 11, 2005

(65) Prior Publication Data

US 2006/0104992 A1    May 18, 2006

(51) Int. Cl.
*A61K 38/04* (2006.01)
*A61K 38/10* (2006.01)
*A61K 38/17* (2006.01)
*C07K 7/04* (2006.01)
*C07K 7/08* (2006.01)
*G01N 33/53* (2006.01)

(52) U.S. Cl. .................. 530/327; 530/300; 435/183; 435/174; 435/5; 435/7.1

(58) Field of Classification Search .................. 530/300
See application file for complete search history.

(56) References Cited

U.S. PATENT DOCUMENTS

| | | | |
|---|---|---|---|
| 5,002,766 A | 3/1991 | Ransberger et al. | |
| 5,436,143 A | 7/1995 | Hyman | |
| 5,872,210 A | 2/1999 | Medabalimi | |
| 6,165,794 A | 12/2000 | Craik et al. | |
| 6,534,310 B1 | 3/2003 | Craik et al. | |
| 6,979,566 B2 | 12/2005 | Friedman et al. | |
| 7,244,606 B2 * | 7/2007 | Chou et al. ................. | 435/226 |
| 2002/0192797 A1 | 12/2002 | Dash et al. | |
| 2004/0005557 A1 | 1/2004 | Padigaru et al. | |
| 2004/0005691 A1 * | 1/2004 | Chou et al. ................. | 435/226 |
| 2004/0038330 A1 | 2/2004 | Nagaoka | |

FOREIGN PATENT DOCUMENTS

| | | |
|---|---|---|
| AU | 678202 B | 12/1995 |
| JP | 07316191 | 12/1995 |

OTHER PUBLICATIONS

Xin et al. J. Biol. Chem. 1989, vol. 264, pp. 4482-4489.*
Yoshimasu et al. Protein Expression and Purification, 2002, vol. 25, pp. 229-236.*
U.S. Appl. No. 10/336,512, filed Jan. 29, 2004, Zhabilov.

* cited by examiner

*Primary Examiner*—Bruce Campell
*Assistant Examiner*—Bao Qun Li
(74) *Attorney, Agent, or Firm*—Cislo & Thomas, LLP

(57) ABSTRACT

An isolated antiviral peptide is characterized by the amino acid sequence GDEPLENYLDTEYF and a significant in vitro binding affinity for HIV-1 gp 120 and gp 41, and human CD4 cells. The peptide exhibits anti-retroviral activity in vivo, particularly anti-HIV-1 activity.

7 Claims, 7 Drawing Sheets

Porcine pepsinogen sequence:

MKWLLLLSLV VLSECLVKVP LVRKKSLRQN LIKNGKLKDF LKTHKHNPAS KYFPEAAALI GDEPLENYLD    Pig

IGDEPLENYLD    Pig

TEYFGTIGIG TPAQDFTVIF DTGSSNLWVP SVYCSSLACS DHNQENPDDS STFEATSQEL SITYGTGSMT    Pig
TEYF-45K IPF-P1

GILGYDTVQV GGISDTNQIF GLSETEPGSF LYYAPFDGIL GLAYPSISAS GATPVFDNLW DQGLVSQDLF    Pig
                                                         S  GATPZTE  -30K CP

SVYLSSNDDS GSVVLLGGID SSYYTGSLNW VPVSVEGYWQ ITLDSITMDG ETIACSGGCQ AIVDTGTSLL    Pig
                              NX VPVSVEGYXQ ITLDSITX-15K IPF-P1
           LGGID  SSYYTGSLNW  VPVSVEGYWQ IT-20K CP
                  SYYTGSLNiR  VPVSVEGYWQ ITLDSITM-20K CP
                  SYYTGSLNW   VPVSVEGYWQ ITLDSI-15K CP
                  NW          VPVSVEGYWQ ITLDSITMDG RTI-15K CPL

TGPTSAIAIN IQSDIGASEN SDGEMVISCS SIDSLPDIVF TINGVQYPLS PSAYILQDDD SCTSGFEGNm    Pig

VPTSSGELWI LGDVFIRQYY TVFDRANNKV GLAPVA                                        Pig

GDEPLENYLIDTEW..from 45 kDa band of IPF-P i prep
NXVPVSVEGYXQITLDSITX-from 15 kDa band of IPF-PI prep
SGATPVF-30K CP [CLP]
LGGII7SSYYTGSLNWVPVSVEGYWQIT--20K CP (primary sequence)
SYYTGSLNWVPVSVEGYWQITLSDITM--20K CP (minor sequence)
SAYTGSLNWVPVSVEGYWQITLDSI--15K CP (primary sequence)
NWVPVSVEGYWQITLDSITMDGRTI--15K CP (minor sequence)

FIG. 1

IRREVERSIBLY-INACTIVATED PEPSINOGEN FRAGMENT AND PHARMACEUTICAL COMPOSITIONS COMPRISING THE SAME FOR DETECTING, PREVENTING, AND TREATING HIV

BACKGROUND OF THE INVENTION

Typically, infection with the human immunodeficiency virus, HIV-1, eventually causes acquired immunodeficiency syndrome (AIDS) and an associated syndrome, AIDS-related complex (ARC). Neutralizing this virus has proved difficult, largely because its structure obstructs immune system access to viral epitopes and its genetic material is highly variable. Accordingly, researchers have been seeking prophylactic and therapeutic methods for preventing or controlling HIV which are not dependent upon antibody-mediated immunity.

The HIV retrovirus replicates in certain immune system cells, specifically the CD4+ subset of T-lymphocytes (pre-Th cells arising in the thymus). In the usual course of a cell-mediated immune response to an intracellular pathogen such as a virus, dendritic cells (antigen-presenting cells) carrying antigen fragments and secreted cytokines activate these CD4+ T-cells. Activated cells, called T-helper or Th cells, in turn secrete their own cytokines and stimulate macrophages. CD4+Th cells also propagate cellular immune response by binding chemotactic cytokines (chemokines, CCs) to their CC surface receptors. It is by this route that HIV-1 infection of these cells is enabled because, in addition to binding chemokines, these CC receptors act together with the CD4+ surface glycoprotein as coreceptors for HIV-1 and mediate entry of the virus into the CD4+Th cell. There, the virus usurps the native genetic material for viral replication while destroying cell functions essential for building immunity; the increasing destruction of these cells appears to be responsible for the eventual collapse of the cell-mediated immune system often seen in terminal AIDS patients.

It has been recognized that denying entry into CD4+ cells to the HIV-1 virus could at least slow the progress of the infection and alleviate, if not cure, the disease and/or its symptoms. The complex mechanism by which the virus crosses the cell membrane has been widely investigated. Broadly, the entry of human immunodeficiency virus into, for example, CD4+ Th1 cells (T-helper type 1 cells, is dependent upon a sequential interaction of the gp120/gp41 subunits of the viral envelope glycoprotein gp160 with the CD4+Th1 cell surface glycoprotein and the cell surface receptor CCR5. On binding of gp120 with its cell surface binding sites, a conformational change in the latent gp41 subunit through an intermediate state to an active state is initiated, inducing fusion of the viral and cellular membranes and transport of the virus into the cell (*Nature* 387:426-30, 1997).

Accordingly, numerous binding experiments have been conducted in an effort to find antiviral ligands that will effectively compete with the HIV-1 for CD4+ gp and/or CCR5 binding sites, or that will preferentially block gp120 and/or gp41 binding domains. In one example, a reported structure (X-ray crystallography) comprising a HIV-1 gp120 core complexed with a two-domain fragment of human CD4 and an antigen-binding fragment of a neutralizing antibody that blocks chemokine-receptor binding, is said to reveal a CD4-gp120 interface, a conserved binding site for the chemokine receptor, evidence for a conformational change on CD4 binding, the nature of a CD4-induced antibody epitope, and specific mechanisms for viral immune evasion, "which should guide efforts to intervene" (Nature 393 (6686):632-1, 1998). Also, it has been shown that inhibition of the change in structure of gp41 from its intermediate to active state with peptides used as competitors for critical cell receptors may reduce viral load, and that while gp120 masks epitopes on the gp41 subunit in its latent state, gp41 may be vulnerable to neutralizing antibodies in its transient or intermediate state (Molecular Membrane Biology 16:3-9, 1999). In another study, disclosed in US Patent Application Publication US 2004/0018639 A1, filed Jan. 3, 2003, published Jan. 29, 2004, by Zhabilov et al., the content of which is incorporated herein in its entirety by reference, a protein designated "Thymus Factor" ("TF") is stated to have the ability to bind to a fragment of HIV-1 gp41 in gel electrophoresis, and that this binding property can be used to assay TF activity or in the treatment of HIV.

BRIEF DESCRIPTION OF THE DRAWINGS

Some aspects of the present invention are generally shown by way of reference to the accompanying drawings in which:

FIG. 1 illustrates the porcine pepsinogen sequence (Seq. No. 1 bolded), and major and minor sequences of this pepsinogen;

SUMMARY OF THE DISCLOSURE

Figure 2:
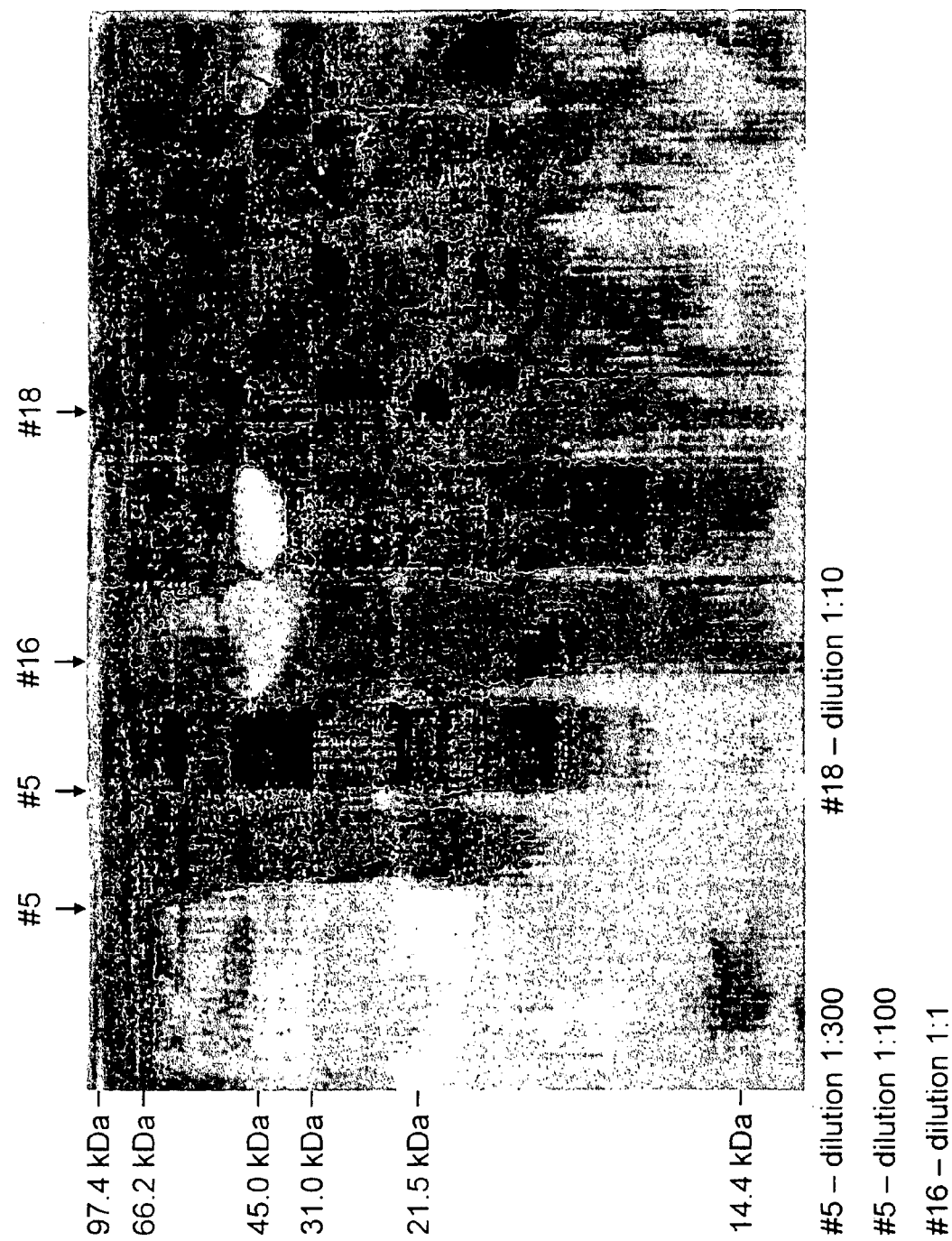
FIG. 2 is a photograph of an electrophoresis gel showing an inactivated pepsinogen fragment ("IPF") in the 45.0 kDa band.

Some embodiments of the present invention are generally directed to providing an isolated antiviral peptide characterized by the amino acid sequence GDEPLENYLDTEYF (SEQ ID:NO 1) and a significant in vitro binding affinity for HIV-1 gp 120, gp 41 and human CD4 cells. The peptide has anti-retroviral activity in vivo, particularly anti-HIV-1 activity. The peptide, referred to herein as IPF (Inactivated Pepsinogen Fragment), was isolated from porcine pepsinogen, purified, and irreversibly inactivated for use in HIV-1 prophylactic, therapeutic and diagnostic procedures.

Other embodiments of the present invention are generally directed to providing pharmaceutical compositions comprising IPF and methods for preventing, treating, and diagnosing HIV-1 infections and HIV-1 related conditions such as AIDS (Acquired Immune Deficiency Syndrome) and ARC (AIDS Related Complex) with these compositions.

DETAILED DESCRIPTION OF THE INVENTION

Pepsins (of which there are several isozymes) are the principal proteases in gastric secretions of adult mammals. They belong to the family of aspartic proteases and are synthesized and secreted by cells in the gastric mucosa as inactive enzyme-precursors consisting of a signal peptide, an activation peptide and an occluded active enzyme. En route to the lumen of the stomach for protein digestion, the signal peptide is cleaved to yield the inactive proenzyme pepsinogen, which, on exposure to a low gastric pH (<4), cleaves in turn to yield mature, catalytically active pepsin.

Porcine pepsin was one of the first enzymes to be studied, and is perhaps the best-understood aspartic protease. It has 327 amino acid (aa) residues, and a molecular mass of 34kDa (PNAS (U.S.) 70:3437-39 1973). Proteolytic activity of pepsin is at its highest at a pH of about 1.8 to 3.5; it is inactivated at a pH of about 5 and irreversibly inactivated (denatured) at a pH of about 6-7. Owing to their importance, amino acid residues associated with the substrate binding (active) site have been a research focal point. However, it is apparently still not clear how much functional activity, if any, is influenced by the remainder of the peptide.

The family of aspartic proteases (aspartases) is characterized by aspartic acid residues at their active (catalytic) sites. Human pepsin, for example, has two active site aspartate residues (coded "D" or "Asp"). This family also includes the HIV protease (and its numerous variants), comprising two identical chains each having a single active-site aspartate residue. Essential for maturation of the newly synthesized virus, which is expressed as a polyprotein, this protease has become a popular target for researchers attempting to block HIV replication.

The peptide of the present invention, characterized by the amino acid sequence GDEPLENYLDTEYF (-Gly-Asp-Glu-Pro-Leu-Glu-Asn-Tyr-Leu-Asp-Thr-Glu-Tyr-Phe-), has been shown to bind in vitro with the gp41 and gp120 subunits of HIV-1 and human CD4 cells, and is expected to have anti-retroviral activity in vivo, particularly inhibition of HIV-1 entry into human CD4+ cells.

Figure 3:
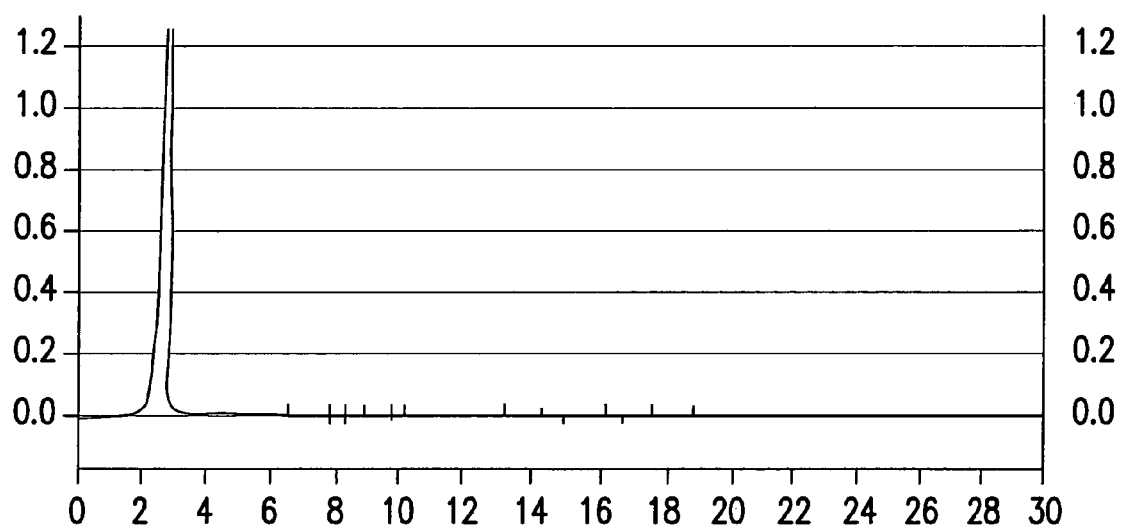
FIG. 3 is a Biacore graph showing a HPLC (High Performance Liquid Chromatography) chromatogram of an isolated IPF in accordance with the present invention.

The exemplified peptide was obtained from porcine pepsinogen (FIG. 1) by isolation from a 45 kDa band of IPF preparation under gel electrophoresis (FIG. 2, Examples hereinbelow). It can also be derived from pepsinogen from any other source containing this sequence, or from any other peptides or proteins containing this sequence whereby suitable source pepsinogens are readily available commercially. Common laboratory methods and reagents for selectively cleaving intact proteins and for isolating and sequencing the cleaved peptides, such as the Erdman degradation process, may be used. The peptide may also be produced by peptide synthesis, using conventional methods. Moreover, genetically engineered constructs expressing the sequence of interest are generally preferred, although chemical syntheses may also be used. The peptides in the IPF fractions may be isolated and concentrated by any one of several techniques well-known to those skilled in the art, such as ammonium sulfate precipitation. The produced peptide isolate may be purified by standard processes such as gel filtration and RP-HPLC, and inactivated, as discussed supra, by exposure to a neutral-to-alkaline environment of about pH 6.5 or greater or as otherwise known in the art. The peptide may also be alkylated to increase immunogenicity if desired, for example, by the process described for methylation of TF in U.S. Patent Application Publication US 2004/0018639 A1, supra. A HPLC chromatogram of the purified, inactivated IPF product of the invention is shown in FIG. 3.

Homologues or analogues of the sequence which conserve at least critical binding site amino acid structures and functions and also conserve any distal structural/functional residues essential for binding activity, as described herein, may be substituted for the IPF of SEQ ID:NO 1. Variants of the sequence, including chemically modified derivatives, having a high sequence similarity will be generally preferred, provided that binding activity is not significantly adversely affected. Residues superfluous to the disclosed function of the peptide of the invention may be deleted or added with the same proviso. Modified sequences may be evaluated for conserved binding activity by, for example, following the binding assays described herein or in the literature. Numerous databanks are accessible for protein sequence analysis, such as those which combine sequence similarity with fold recognition to predict functional equivalents. Binding properties (affinity, specificity, etc.) may also be evaluated by the binding assays described below or other conventional assays, as known in the art.

Figure 4:
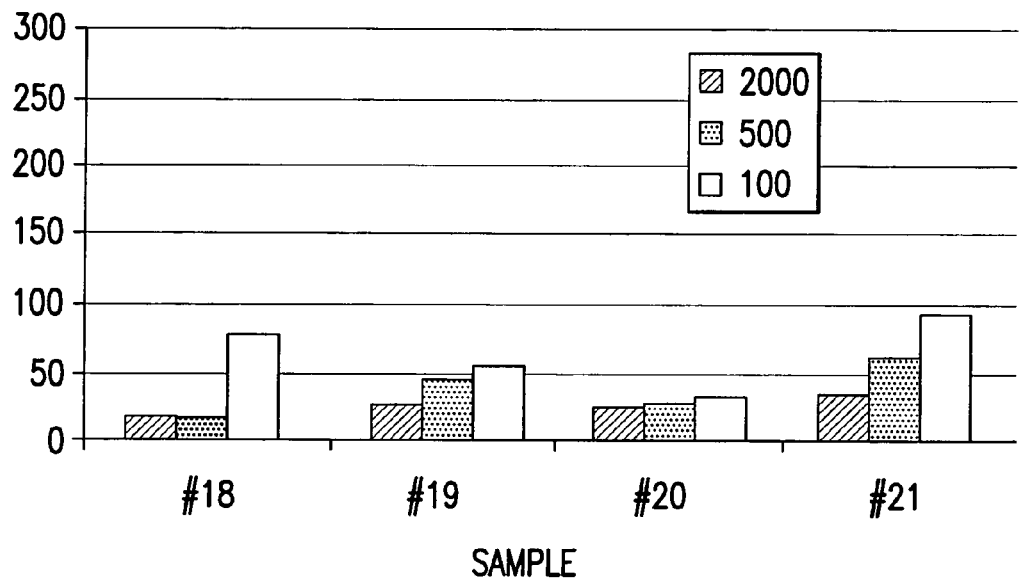
FIGS. 4, 5, 6, and 7 illustrate exemplary binding of four samples of IPF with gp41, gp120, human CD4, and human serum at 3 different dilutions.
Figure 5:
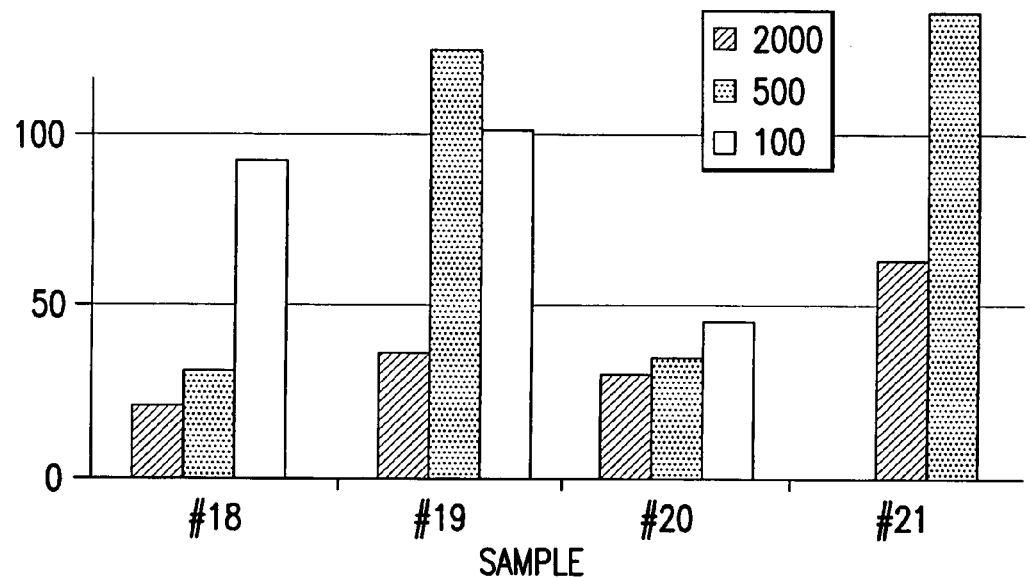
Figure 6:
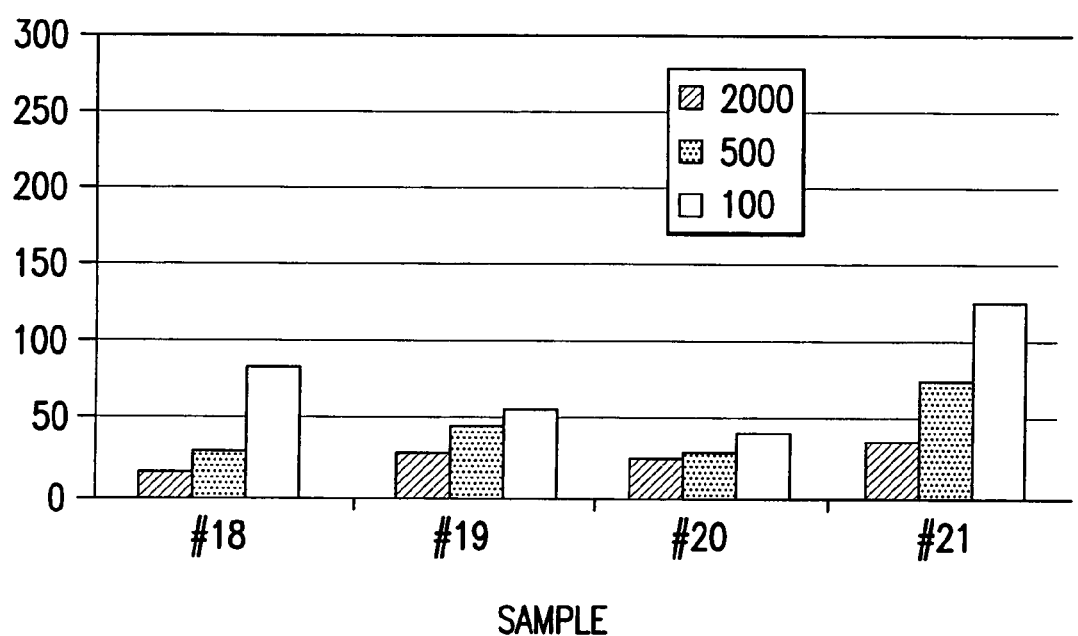
Figure 7:
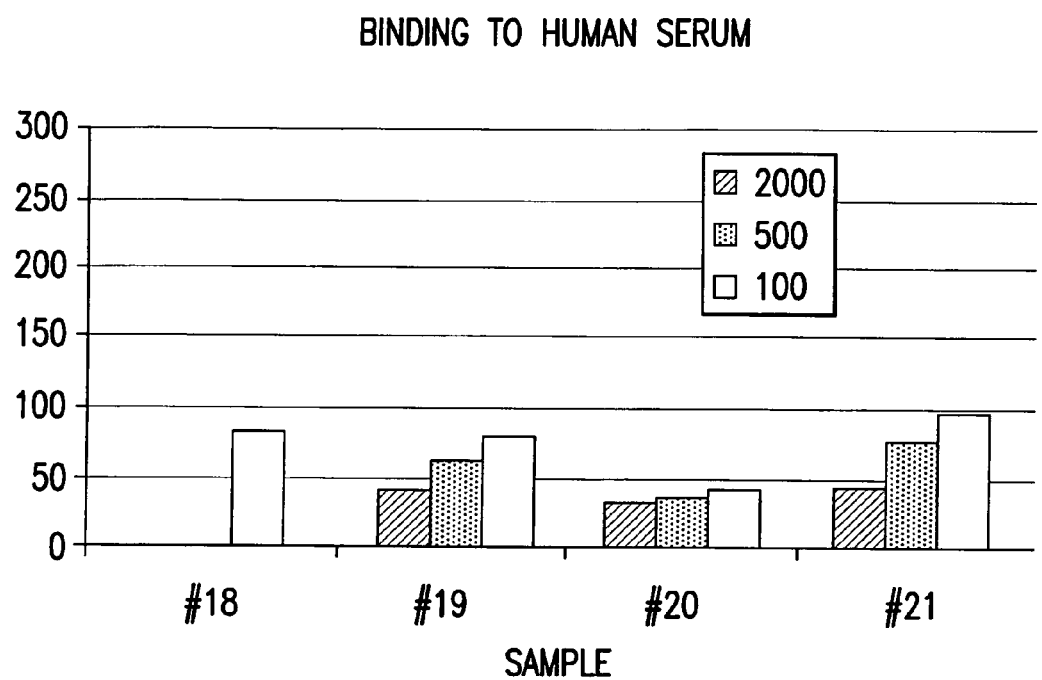
Figure 8:
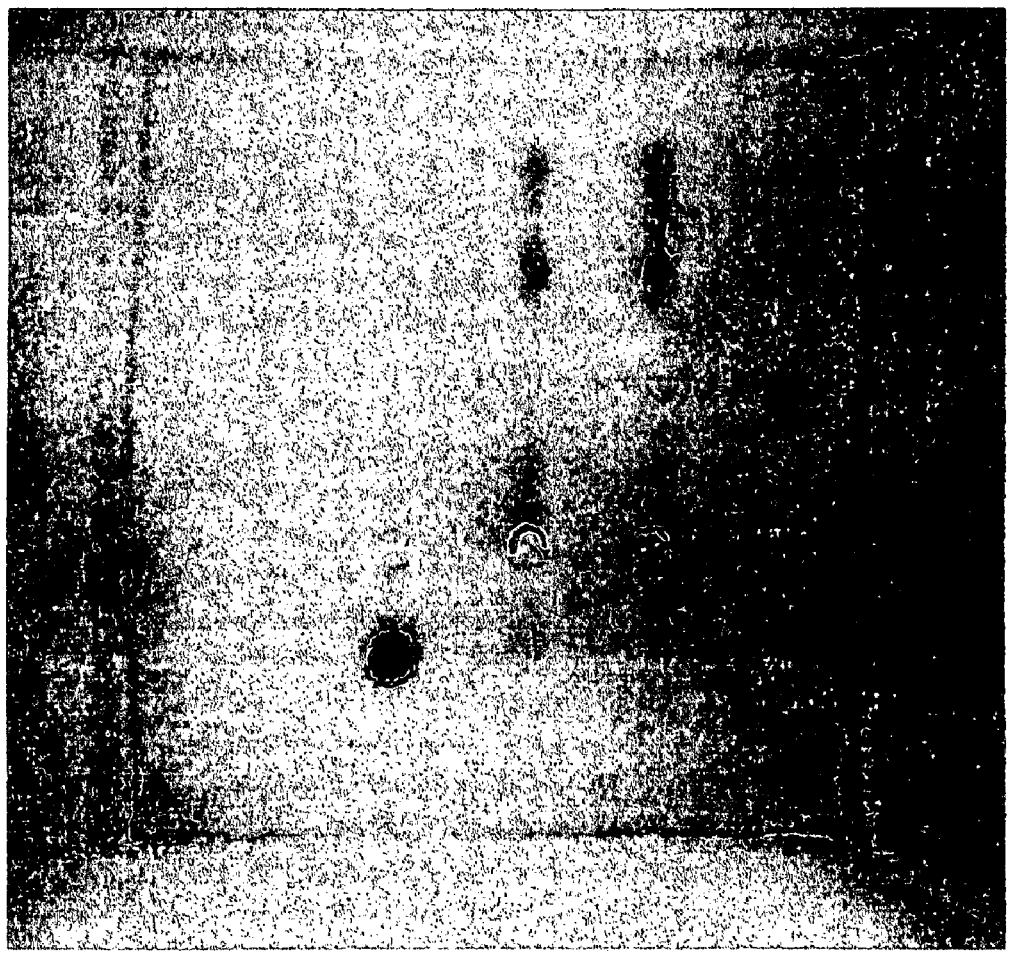
FIG. 8 is a photograph of an electrophoresis agarose gel showing bound IPF and gp41.

IPF demonstrates binding in vitro with nonglycolysed fragment 579-601 of the HIV-1 envelope protein gp41 subunit (FIGS. 4 and 8), with gp120 HIV-1 subunit (FIG. 5), with human CD4+ cells (FIG. 6), and with human serum (FIG. 7) under gel electrophoresis. The spontaneous binding of IPF with the gp41 subunit is a particularly important biological property. Separately, under simple agarose electrophoresis, IPF and gp41 move in opposite directions. However, when they are mixed prior to electrophoresis, gp41 changes direction and takes the direction of IPF. Quantitative analysis showed that the binding capacity ratio of IPF to gp41 was 1:0.66. That is, three molecules of IPF bound two molecules of gp41 to form a complex which may function in vivo as, for example, a superantigen with significant anti-HIV-1 biological activity. Such antigen can be used as a bioassay reagent, in the production of mono- or polyclonal antibodies, in the manufacture of vaccines, and in other applications wherein antigens are conventionally employed. While the mechanism of these binding events is not completely understood at this time, it is contemplated that exposure of HIV-1 to the IPF of the present invention will effectively block gp41 and gp120 domains essential for viral entry into CD4+ cells and inhibit viral infection, in vivo and in vitro. It is also contemplated that the IPF of the present invention will effectively compete with HIV-1 for its CD4+ cell surface binding sites and inhibit virus entry into these cells, in vivo and in vitro. Various in vitro protocols are known in the art for predicting in vivo antiviral activity of compounds for inhibiting replication of HIV, and these protocols may be used in connection with the practice of the present invention. Exemplary art-recognized anti-HIV screening assays are cited in U.S. Pat. No. 5,869,522, issued 9 Feb. 1999 to Boyd et al., including those described in *J.Virol.Methods,* 33:87-100,1991; *J.Natl.Cancer Inst.,* 81:577-586, 1992; and *J.Med.Chem.* 35:1978-1986, 1992, and Boyd, M. R., in *AIDS Etiology: Diagnosis, Treatment, and Prevention,* pp305-319 (Lippincott, 1988, DeVita, V. T., Jr., et al., eds). In accordance with one aspect of the present invention, IPF is used to diagnose viral infection, particularly HIV-1 infection. Bioassays suitable for this purpose are well-known and routine. Typical of these are assays based on competitive binding between, for example, a known amount of a viral protein and a biological sample to be tested for the same viral protein, using an excess of antiviral reagent capable of specifically binding with the known protein, such as an antibody. A mixture of these is incubated and the amount of bound complex calculated and compared to that in a control mixture lacking the sample. The presence, if any, and amount of the viral protein in the sample can then be determined. There are numerous variations on this process, such as sandwich assays, assays with immobilized reagent, assays using labeled reagent (e.g., ELISA, RIA, FIA), and so on. Whatever the variation, whether for detecting or quantifying complex, or for additional reagents, or other modification, they all require a binding agent for the unknown sample. Any of these routine binding assays for quantifying or identifying an unknown sample may thus be used in the practice of the present invention by substituting IPF as the antiviral binding agent for samples to be tested for HIV-1 gp120, gp41, or infected CD4+T- cells.

In accordance with another aspect of the present invention, IPF is used as a prophylactic or therapeutic to prevent or to treat HIV infections. (Herein the term "HIV infections" refers to AIDS and ARC in addition to viral infection per se unless otherwise noted). For in vivo use, IPF may be prepared for administration by mixing it at the desired degree of purity with a pharmaceutically-acceptable carrier suitable for the route of administration, as well-known in the art. Although IPF is desirably administered with an adjuvant in some applications, in situations where a series of IPF doses are administered, boosters with IPF may not require adjuvant. Intramuscular or subcutaneous injections are presently the contemplated route for both therapeutic and prophylactic administration of IPF. However, intravenous delivery, delivery via catheter or other surgical tubing, or other parenteral route may also be used. Alternative routes include oral routes for administering tablets, liquid formulations and the like, as well as inhalation routes. Liquid formulations reconstituted from powder formulations may be utilized. IPF may also be administered via microspheres, liposomes, or other microparticulates, and via delivery systems or sustained release formulations dispersed in certain tissues including blood.

The dosage of IPF administered will depend upon the properties of the formulation employed, e.g., its binding activity and in vivo plasma half-life, the concentration of IPF in the formulation, the administration route, the site and rate of dosage, the clinical tolerance of the patient involved, the patient's condition, and other considerations, as known in the art. Different dosages may be utilized during a series of sequential treatments. The practitioner may administer an initial dose and then boost with relatively smaller doses of IPF. The dosages of IPF may be combined with other HIV antivirals, such as AZT.

The following is an example of a contemplated IPF formulation, dosage and administration schedule:

The patient is administered an intramuscular injection containing 8 mg of IPF (preferably 2 ml of a formulation containing 6 mg/ral of IPF in a pharmaceutically acceptable solution) or 57 μg of IPF protein per kg body weight of the patient. Each treatment course consists of 16 injections, with two injections on consecutive days per week for 8 weeks. Three months after the last injection, if the patient's condition warrants, the treatment regimen is repeated. The treatment regimen may be repeated until satisfactory results are obtained, e.g., a halt or delay in the progress of the infection or disease, an alleviation of the infection or disease, or a cure is obtained. Preferably, in this application, IPF will be formulated with an aluminum hydroxide (Al(OH)3) adjuvant. Aluminum hydroxide is a widely used adjuvant, especially in commercial products such as vaccines. It is well suited for strong antigens. Many sources of aluminum hydroxide are available. The adjuvant is commercially available under the trade name Alhydrogel® by Accurate Chemical & Scientific Co. of Westbury, N.Y. In one example, the final 1 ml of the final IPF formulation may contain: 4 mg IPF (purity > 96% ±0.290); 2.26 mg 0.016M $AlPO_4$ (or 0.5 mg $Al^{+3}$); 4.1 mg 0.004M $CH_3COONa$; and 12.9 mg $C_6H_5O_7$ (sodium citrate); pH 6.2. In one regimen, 2 ml of this formulation makes up one vial with the dosage per patient per day being 16 vials. During the regimen, the patient should be monitored to assess the effectiveness of the regimen. CD+4 cell counts are useful and common methodology for evaluating HIV infection, as are assays for antibody or T-cell titers.

EXAMPLES

Isolation and Purification of Irreversibly-Inactive Pepsin Fraction

The following Examples show the isolation, purification, and characterization of IPF from active pig pepsinogen. Also illustrated is IPF binding activity.

Example I

Isolation and Inactivation of Pepsinogen Fragment

All the buffers and solutions used in this section were sterilized by filtration. If needed, the buffers (0.2 N or 0.1 N HCl) were used to adjust the solutions. All the chemicals, including the distilled water, for the preparation of the buffers and solutions were USP Grade. The ratio of the pepsin to the buffers was 1:4 (weight/weight).

IPF was isolated from active pepsin (Sigma 1:10000) by ammonium sulfate precipitation with centrifugation at 4° C. The lyophilized pepsin powder was dissolved in 0.14M sodium chloride (NaCl), 0.05M sodium acetate ($CH_3COONa$ . $3H_2O$), 0.05M sodium citrate ($C_6H_5O_7Na_2.2H_2O$), and 0.20N HCl (pH 2.8-3.2) buffer. The pH of the active pepsin suspension was then increased to 6.2-6.6 and the suspension was incubated for 30 minutes. The suspension was then precipitated with a saturated solution of $(NH_4)_2SO_4$. After degradation, the mixture was centrifuged (8000 RPM at 4° C.) for 60 minutes and the supernatant discarded. The pellet was dissolved in a minimum quantity of 0.14M NaCl, and the resulting solution was dialyzed for 18 hr against dialysis buffer: 0.1M NaCl, 0.1M sodium acetate, and 0.02M thimerozal USP, pH 6.8.

Example II

Purification and Recovery of Irreversibly Inactivated Pepsinogen Fragment

The purification of IPF included the following steps: dialysis, centrifugation, gel filtration, and reversed phase HPLC.

After dialysis, the low molecular weight dialysate was centrifuged at 15,000 rpm at 4° C. for 60 minutes (Beckman rotor) with precipitation of the residual ammonium sulfate. The product was purified by gel filtration to recover purified IPF from the crude mixture, and then purified by filtration on Bio-gel P10 or Sephadex G-75 gels (from Pharmacia Uppsala, Sweden), or 0.2μ SFCA membrane (Nalgene Labware, Rochester, N.Y.). Further purification was achieved by reversed phase high-performance liquid chromatography in an RP-HPLC system GOLD (Beckman) on C-18 columns (RP Ultrasphere 10 mm Spherical 80 A Preparative 21.2×150 mm) using gradient 30% acetonitrile diluted in sterile water, HPLC-grade at 15% methanol HPLC-grade mobile phase. Detection 254 nm; flow rate 0.850 ml/min., solvent at pH 6.8. The final purification step included sterile filtration with Nalgen filters 0.45μ. The HPLC elution profile of the product showed one isolated peak, IPF (see FIG. 3).

Example III

Determination of Molecular Weight

Molecular weight was determined by silver stained 13% non-reducing SDS-PAGE using the Laemmli method (*Nature* 227-680, 1970). The molecular weight standard demonstrated one peptide with a molecular weight of 45.000 KD (FIG. 2). This band was isolated, and HPLC chromatogram (FIG. 3) confirmed a single peptide in the band.

Example IV

Assessment of Binding Activity

Samples of IPF (#18, 19, 20, and 21) were used to detect binding with gp120, gp41, CD4+ cells, and serum from a healthy patient. New chips were coated with these proteins and Biacore assays for binding activity were performed. These samples were diluted to 1:2000, 1:500 and 1:100. The results are shown in FIGS. 4, 5, 6, and 7. Sample #21 bound to all target proteins better than the other samples. The assay used a Biacore (Biacore AB, Uppsala, Sweden) system based on sensor chips which provide surface conditions for attaching molecules of interest, a microfluidic flow system for delivering samples to the surface, and a surface plasma response (SPR) which detects mass concentration at the surface. SPR-based biosensors monitor interactions by measuring the mass of molecules bound to the surface. This response is expressed by resonance units (RU), whereby a change in concentration of 1 pg/mm is equivalent to a change of 0.0001 in the angle of intensity minimum, which equals one RU. The exact conversion factor between RU depends upon the properties of the sensor surface and the nature of the molecule responsible for the change in concentration. The assays demonstrate the formation of superantigen for provoking immune response.

Example V

UV Absorption

Circular dichroism (CD) provides information about the secondary structure of optically active materials. The far-UV or amide region (170-250nm) is dominated by contributions of the peptide bonds, whereas CD bands in the near-UV region (250-300nm) originate from the aromatic amino acids. The UV region of IPF was in the range of 252-260 nm.

A person skilled in the art would appreciate that exemplary embodiments described hereinabove are merely illustrative of the general principles of the present invention. Other modifications or variations may be employed that are within the scope of the invention. Thus, by way of example, but not of limitation, alternative configurations may be utilized in accordance with the teachings herein. Accordingly, the drawings and description are illustrative and not meant to be a limitation thereof.

Moreover, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Thus, it is intended that the invention cover all embodiments and variations thereof as long as such embodiments and variations come within the scope of the appended claims and their equivalents.

What is claimed is:

1. An isolated peptide with antiviral efficacy consisting of the amino acid sequence of SEQ ID NO: 1, said peptide having substantial in vitro binding affinity for human immunodeficiency virus type-1 (HIV-1), gp 120, HIV-1 gp 41 and HIV-1 infected human CD4 cells.

2. A composition including a carrier and a peptide with antiviral efficacy, said peptide consisting of the amino acid sequence of SEQ ID NO: 1 and having substantial in vitro binding affinity for HIV-1 gp 120, HIV-1 gp41 and HIV-1 infected human CD4 cells.

3. A complex of the peptide of claim 1 with HIV-1 gp41, HIV-1 gp120, or HIV-1 infected human CD4+ cells.

4. A complex of the peptide of claim 1 with HIV-1 gp41.

5. A complex of the peptide of claim 1 with HIV-1 gp120.

6. A composition comprising a carrier and the complex of claim 4.

7. A composition comprising a carrier and the complex of claim 5.

* * * * *

```
                         SEQUENCE LISTING

<160> NUMBER OF SEQ ID NOS: 1

<210> SEQ ID NO 1
<211> LENGTH: 14
<212> TYPE: PRT
<213> ORGANISM: Sus domesticus
<220> FEATURE:
<221> NAME/KEY: misc_feature
<223> OTHER INFORMATION: Peptide sequence isolated from porcine
      pepsinogen

<400> SEQUENCE: 1

Gly Asp Glu Pro Leu Glu Asn Tyr Leu Asp Thr Glu Tyr Phe
1               5                   10
```